United States Patent [19]

Steer et al.

[11] Patent Number: 4,534,766
[45] Date of Patent: Aug. 13, 1985

[54] DRAINAGE BAG FOR URINE AND SUPPORT THEREFOR

[75] Inventors: Peter L. Steer; John V. Edwards, both of East Grinstead, England

[73] Assignee: Craig Medical Products Limited, East Grinstead, England

[21] Appl. No.: 482,669

[22] Filed: Apr. 6, 1983

[30] Foreign Application Priority Data

Apr. 16, 1982 [GB] United Kingdom ................ 8211103

[51] Int. Cl.³ .............................................. A61M 1/00
[52] U.S. Cl. .................... 604/323; 604/335; 604/350; 248/95
[58] Field of Search ....... 128/760, 767, 769, DIG. 24; 604/317, 322–326, 335, 350; 248/95, 100; 383/13, 15, 9, 23

[56] References Cited

U.S. PATENT DOCUMENTS

| 2,788,822 | 4/1957 | Parker | 383/9 |
| 3,529,599 | 9/1970 | Folkman | 128/275 |
| 3,740,770 | 6/1973 | Villari | 604/325 |
| 4,194,715 | 3/1980 | Forman et al. | 248/311.2 |
| 4,312,352 | 1/1982 | Meisch et al. | 604/322 |
| 4,447,939 | 5/1984 | Taylor | 604/322 |

Primary Examiner—C. Fred Rosenbaum
Assistant Examiner—J. L. Kruter
Attorney, Agent, or Firm—Lawrence S. Levinson; Sanford J. Asman

[57] ABSTRACT

A drainage bag includes front and rear walls of plastics material and is combined with a support. The walls are welded together along their top edges in such a way as to define a plurality of linearly-spaced through holes which do not communicate with the interior of the bag. These holes are capable of accepting hooks or studs on a support (or hanger) separate from the bag. The support has spaced hooks or studs constructed to be respectively received in the holes.

The hanger may be molded in one piece of synthetic plastic.

2 Claims, 3 Drawing Figures

DRAINAGE BAG FOR URINE AND SUPPORT THEREFOR

BACKGROUND OF THE INVENTION

The present invention relates to a drainage bag. In particular, it relates to a drainage bag for urine and a support therefor.

Many designs for drainage bags are known. In hospitals, it is often necessary to hang drainage bags on a suitable support. For this purpose, holes are often provided in an upper region of the bag. An example is shown in British Patent Specification No. 1 027 288. U.S. Pat. No. 3,529,599 describes a drainage bag having a handle permanently joined to the top of the bag. This type of arrangement is not desirable as it is expensive, to provide a handle with each bag. Also, in use, a conventional internal flap valve may become inadvertently closed off if the bag is kinked or folded.

It would be desirable to provide an improved drainage bag and support therefor.

SUMMARY OF THE INVENTION

According to the present invention, there is provided, in combination, a drainage bag and a support therefor. The bag includes front and rear plastic walls which are welded together along their top edges in such a way as to define a plurality of linearly-spaced through holes which do not communicate with the interior of the bag and which are capable fo accepting hooks of studs on a support or hanger separate from the bag. The bag is characterized in that the support has spaced hooks or studs constructed to be respectively received in the holes.

Also, according to the invention, there is provided a hanger for supporting a drainage bag characterized in that the hanger is molded from plastic in one piece, and it includes a handle portion and a bar portion carrying hooks or studs projecting therefrom. The bar portion is preferably straight.

Further, according to the invention, there is provided a support or hanger for supporting a bag characterized firstly by fixing means whereby it can be temporarily attached to a drainage bag which has holes in a linear array in its upper region, and secondly by an apertured tongue located to extend downwardly and centrally behind or in front of the bag. The function of the tongue is to prevent the flaps of an anti-reflux valve, e.g. a conventional flap valve in the bag from being kinked thereby preventing the valve from becoming closed off if, for example, the bag is placed in a position where it would otherwise be folded or kinked.

According to a preferred feature of the present invention, a drainage bag as defined above also has an outlet tap of the type disclosed and claimed in U.S. Pat. No. 4,462,510 entitled TAP FOR DRAINAGE BAG, which issued to P. L. Steer et al. on July 31, 1984, the contents of which are hereby incorporated by reference.

The hanger is preferably molded in one piece from a plastic, such as polypropylene. It may be constructed with a fold-over tab defining a recess in which a drainage tube may be located. Such a tab serves as a tube guide and ensures that the tube direction just above the bag is substantially vertically downward.

The bar portion of the hanger preferably has four hooks upon which, in use, the bag may be hung.

DETAILED DESCRIPTION OF AN EXEMPLARY EMBODIMENT

Figure 1:
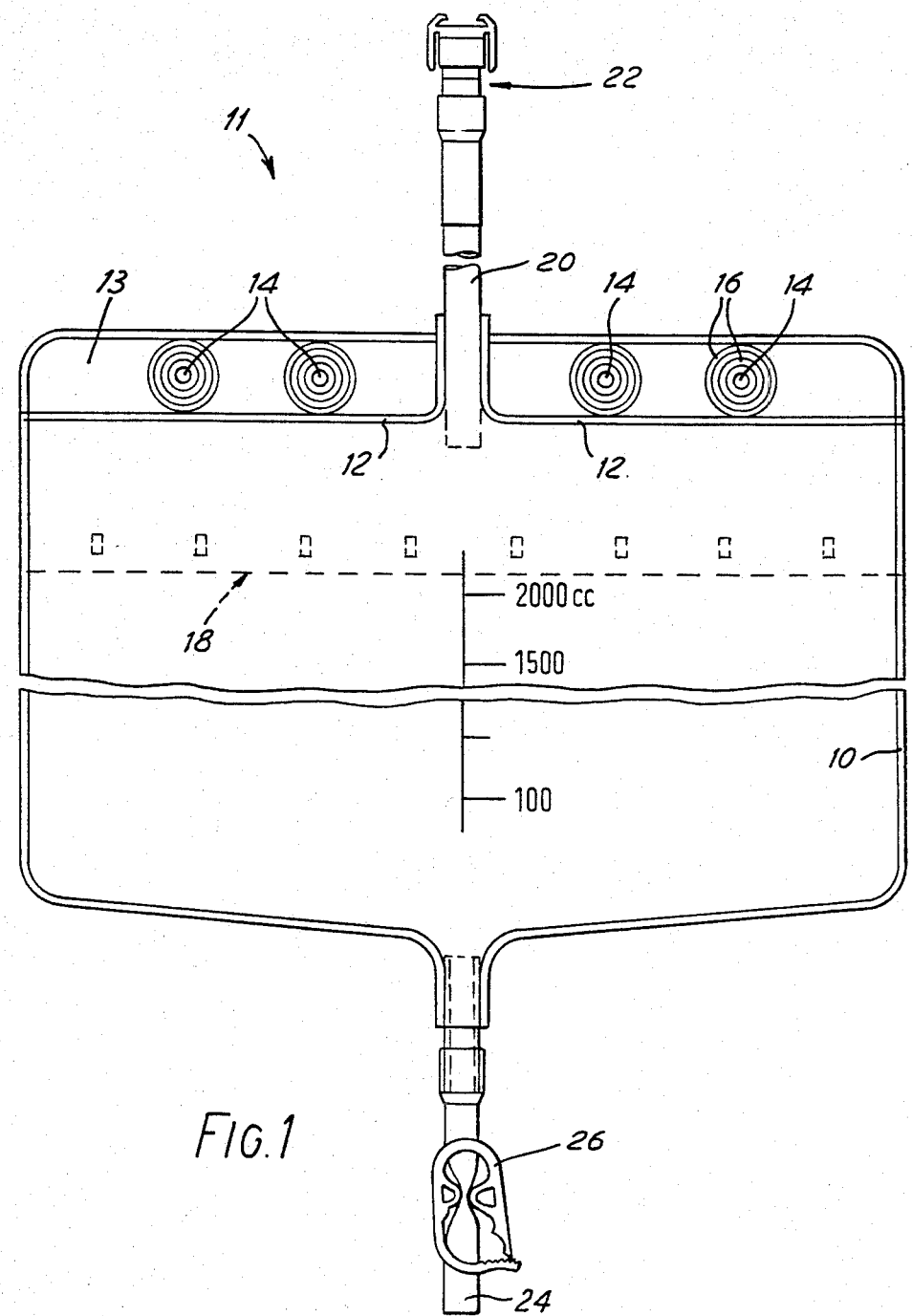
FIG. 1 is a front elevation of one embodiment of drainage bag according to the invention.

The urine bag 11 illustrated in FIG. 1 has front and rear walls comprised of plastics material, e.g. 0.006 inch thick PVC (polyvinyl chloride), welded together by a tramline weld 10 around the periphery. An extra weld 12 defines with the weld 10 an upper region 13 of the bag 11. The space between the walls in this region does not communicate with the interior of the bag 11. Four holes 14, each surrounded by a pair of concentric circular strengthening welds 16, are provided in the upper region of the bag.

The illustrated bag 11 has an internal anti-reflux valve 18 of the type conventionally used. As an alternative, an anti-reflux valve of the kind disclosed and illustrated U.S. Pat. No. 4,462,510, in the contents of which are hereby incorporated by reference.

A drainage tube 20 extends to the top of the bag 11 and is fixed thereto in a liquid-tight manner. The tube 20 preferably has a tube coupling 22 thereon of the type described in copending U.S. patent application Ser. No. 336,479 now abandoned entitled TUBE COUPLING, filed Dec. 31, 1981 now U.S. Pat. application Ser. No. 599,132 filed Apr. 11, 1984, the contents of which are hereby incorporated by reference.

An outlet tube 24 extends from the bottom of the bag 11 and this may carry a separate clip 26. The illustrated clip 26 is of a type known in the art as HALKEY-ROBERTS clip. As a preferable alternative, the bag may have an outlet tap of the type described in copending U.S. Pat. No. 4,462,510.

Figure 2:
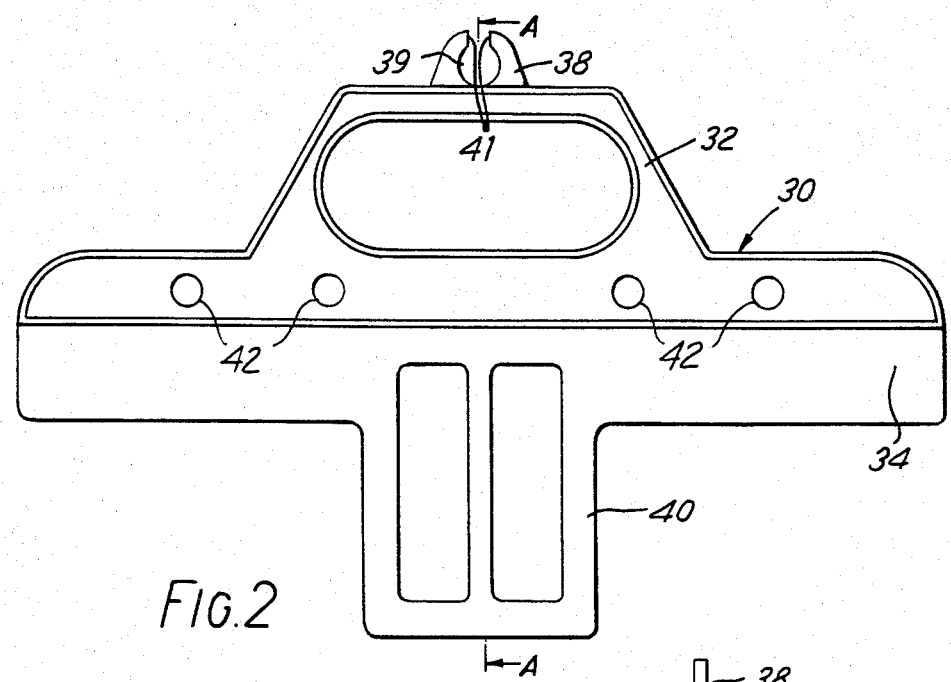
FIG. 2 is a front elevation of a bag support or hanger suitable for use with the bag of FIG. 1.
Figure 3:
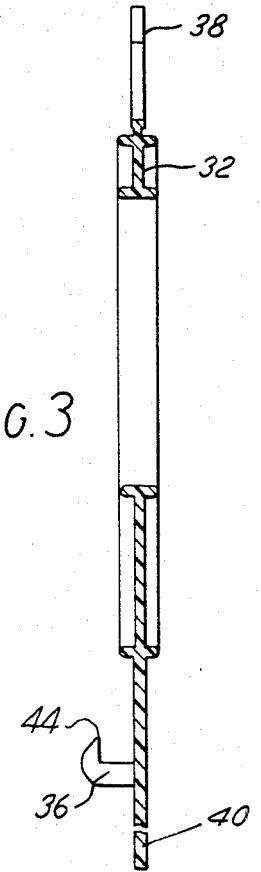
FIG. 3 is a cross-section on the line A—A in FIG. 2.

The bag support or hanger 30 illustrated in FIGS. 2 and 3 has a handle portion 32, a bar portion 34, four hooks 36, a fold-over tab 38, and a flat tongue 40 all molded in one piece from polypropylene. Other materials, e.g. plastics, wood, metal or thick cardboard could also be used. The bar portion 34 has four hooks 36 therein which may be used for hanging up the bag. The hooks 36 are spaced to correspond with the holes 14 and each one has a sharp upwardly-directed point 44. In use, the hooks 36 are pushed through the corresponding holes 14, whose diameter may be chosen so that the hooks 36 slightly split the plastic of the bag, leading to a secure attachment of the hanger or support 30 to the bag 11. Once a bag 11 is full, it can readily be removed and a new bag 11 fitted. It is sufficient to supply one hanger or support 30 with each pack of 10 or 20 bags, thereby leading to substantial savings in material and manufacturing costs.

In use, the tab 38 serves as a tube guide and holder, the shape and size of its recess 39 being chosen in relation to the tube 20. The tab is bent over so that it is approximately horizontal and the tube is pushed past the ears 41 into the recess 39.

We claim:

1. A combined urine drainage bag and support therefor comprising:
   (a) a bag having front and rear plastic walls with elongated top edges, said walls being welded together along their top edges in such a way as to define a plurality of reinforced, linearly-spaced through holes which do not communicate with the interior of said bag and which are capable of accepting hooks or studs on a hanger separate from said bag, an inlet tube in said top edges communicating with the interior of said bag and terminating in an anti-reflux valve within said bag; and (b) separate support means having a transverse portion supporting linearly-spaced hooks, said hooks removably received in said holes of said bag, whereby a single support means can be simultaneously used with a plurality of bags, said support means characterized by an apertured tongue means located to extend downwardly behind or in front of said bag, said tongue having a downward extending length which is greater than the length of the transverse portion of said support means, whereby said tongue means prevents the flaps of an anti-reflux valve, from being kinked and so prevents said valve from becoming closed off should said bag be placed in a position where said flaps otherwise would have been folded or kinked.

2. The combination according to claim 1 wherein said separate support means extends vertically above the top edges of the bag and includes a fold-over tab defining a recess in which a drainage tube may be located, said tab being constructed and arranged to serve as a tube guide to ensure that the tube direction just above the bag is substantially vetically downward.

* * * * *